United States Patent
Bartha et al.

(10) Patent No.: US 6,511,473 B2
(45) Date of Patent: Jan. 28, 2003

(54) IMPLANTABLE BIOARTIFICIAL ACTIVE SECRETION SYSTEM

(75) Inventors: John M. Bartha, Rancho Palos Verdes, CA (US); Lehel Balint, Rancho Palos Verdes, CA (US); Gregory Zeltser, Irvine, CA (US); Arthur Bunzel, Laguna Beach, CA (US); Yin S. Tang, Los Angeles, CA (US)

(73) Assignee: Biodepo, Inc., Anaheim, CA (US)

( * ) Notice: Subject to any disclaimer, the term of this patent is extended or adjusted under 35 U.S.C. 154(b) by 44 days.

(21) Appl. No.: 09/772,702

(22) Filed: Jan. 30, 2001

(65) Prior Publication Data

US 2002/0103475 A1 Aug. 1, 2002

(51) Int. Cl.⁷ .................................................. A61K 9/22
(52) U.S. Cl. .............................. 604/891.1; 604/890.1; 604/892.1
(58) Field of Search .................... 604/890.1, 891.1, 604/892.1, 153, 93.01; 623/23.64, 23.65

(56) References Cited

U.S. PATENT DOCUMENTS

| | | | | |
|---|---|---|---|---|
| 4,378,016 A | * | 3/1983 | Loeb | 128/260 |
| 4,411,651 A | * | 10/1983 | Schulman | 604/151 |
| 4,493,697 A | * | 1/1985 | Krause et al. | 604/50 |
| 4,496,343 A | * | 1/1985 | Prosl et al. | 604/86 |
| 4,544,329 A | * | 10/1985 | O'Boyle | 417/53 |
| 4,838,887 A | * | 6/1989 | Idriss | 604/891.1 |
| 5,011,472 A | * | 4/1991 | Aebischer et al. | 604/50 |
| 5,116,493 A | * | 5/1992 | Chick et al. | 210/192 |
| 5,183,472 A | * | 2/1993 | Jaehrling et al. | 604/284 |
| 5,262,055 A | * | 11/1993 | Bae et al. | 210/645 |
| 5,324,518 A | * | 6/1994 | Orth et al. | 424/423 |
| 5,387,237 A | * | 2/1995 | Fournier et al. | 604/175 |
| 5,554,148 A | * | 9/1996 | Aebischer et al. | 604/890.1 |
| 5,855,616 A | * | 1/1999 | Fournier et al. | 623/11 |
| 5,993,414 A | * | 11/1999 | Haller | 604/93 |
| 6,238,367 B1 | * | 5/2001 | Christiansen et al. | 604/93 |

OTHER PUBLICATIONS

The DCCT Research Group: The effect of intensive treatment of diabetes on the development and progression of long–term complications in insulin–dependent diabetes mellitus. N. Engl. J. Med., 329:977–986, 1993.

Christopher D. Saudek: Novel Forms of Insulin Delivery. Endocrinol. Metab. Clinic North Am., 26, 599–610, 1997.

Helene Hanaire–Broutin, Christiane Broussolle, Nathalie Jeander, Eric Renard, Bruno Guerci, Marie Joelle Haardt et al: Feasibility of Intraperitoneal Insulin Therapy with Programmable Implantable Pumps in IDDM. Diabetes Care, 18:388–392, 1995.

(List continued on next page.)

*Primary Examiner*—Henry C. Yuen
*Assistant Examiner*—Frederick C. Nicolas
(74) *Attorney, Agent, or Firm*—Stetina Brunda Garred & Brucker (57) ABSTRACT

An implantable bioartificial active secretion system for providing a physiological secretion such as insulin necessary for functionality of a physiologic activity such as glucose metabolism of a living-being host. The system includes a housing implantable within the host in fluidic communication with tissue fluid indicative of secretion need. A chamber within the housing contains a plurality of physiologically active, autonomously functioning, live secretory cells for producing the physiological secretion. A periodically operating pump apparatus moves tissue fluid into contact with the secretory cells for pick up of the regulating physiological secretion for subsequent physiologically-effective dispensing into the host while avoiding immunorejection of the host body or of the host to the secretory cells.

42 Claims, 3 Drawing Sheets

OTHER PUBLICATIONS

David M. Nathan, Frederick L. Dunn, John Bruch, Charles McKitrick, Mary Larkin, Coral Haggan et al: Postprandial Insulin Profiles with Implantable Pump Therapy May Exlain Decreased Frequency of Severe Hypoglycemia, Compared with Subcutaneous Regimens, in Insulin–Dependent Diabetes Mellitus Patients. Am. J. Med., 100, 412, 1996.

K. Cochrum, S. Jemtrud, R. Dorian: Successful Xenografts in Mice with Microencapsulated Rat and Dog Islets. Transplant Proc. 27, 6:3297–3301, 1995.

W.B. Jolley, D.B. Hinshaw, T.W. Call, L.S. Alvord: Xenogenic Pancreatic Islet Transplantation in Proteolytic Enzyme–Bonded Diffusion Chambers in Diabetic Rats. Transplant Proc. 9, 363, 1977.

W. Arendarczyk, C. Wojcikowski, M. Gembal, J. Druzynksa: Isogenic, Allogenic and Xenogenic Transplantation of Isolated Pancrease Islets in Rats During Pregnancy. Diabetes 38 (Suppl I), 297, 1989.

Tobias D.C. Zekron, Andrea Horcher, Ulrike Siebers, Konrad Federlin Reinhard G. Bertzel: Synergistic effect of microencapsulation and immunoalteration on islet allograft survival in bioartificial pancreas. J. Mol Med 77: 193–198. 1999.

C. Delunay, S. Darquy, J. Honiger, F. Capron, C. Rouault, G. Reach: Glucose–Insulin Kinetics of a Bioartificial Pancreas Made of an AN69 Hydrogel Hollow Fiber Containing Porcine Islets and Implanted in Diabetic Mice. Artificial Organs, 22(4):291–299. 1998.

Nan–Kuang Yao, Liang–Wey Chang, Boniface Juisiang Lin, Te–Son Kuo: Dynamic aspects for interislet synchronization of oscillatory insulin secretions. Am.J. Physiol., 272, E981–988, 1997.

A. Horcher, T. Zekom, U. Siebers, G. Glock, H. Frank. R. Houben et al: Transplantation of Microencapsulated Islets in Rats: Evidence for Induction of Fibrotic Overgrowth by Islet Alloantigens Released from Microcapsules. Transplant Proc. 26,784,1994.

Stephen K. Hunter, Ye Wang, V.G.J. Rodgers: Bioartificial Pancreas Use in Diabetic Pregnancy. ASAIO Journal, 43:13–17. 1999.

T.Zekron, H. Entenmann, A. Horcher, U. Sieers, G. Glock., U. Zimmermann et al: Lymphoid activation by mcro– and macroencapsulated islets during mice lymphocyte islet culture. Acta Diabetologica 30, 238, 1993.

T. Mandrup–Poulsen, K. Bendtzen, J. Nerup, J. Egeberg, J.H. Nielsen: Mechanism of Pancreatic Islet Cell destruction. Allergy, 41, 250, 1986.

Paul E. Lacy, Edward H. Finke: Activation of Intraislet Lymphoid Cells Causes destruction of Islet Cells. Am. J. Pathol., 138, 1183, 1991.

Steven V. Edelman: Importance of Glucose Control. Prevention and Treatment of Diabetes and its Complications. (1998)–4. 82:665–687.

M. Egger, G. Davey Smith, C. Stettler, P. Diem: Risk of Adverse Effects of Intensified Treatment in Insulin–dependent Diabetes Mellitus: A Meta–analysis. Diabetic Medicine (1997) 14:919–928.

Robert Udelsman, Herbert Chen, Kimberly Loman, Henry A. Pitt, Christopheer D. Saudeck: Implanted programmable insulin pumps: One hundred fifty–three patient years of surgical experience. Surgery (1997)–122. 6:1005–1011.

Jacob Jaremko, Otto Rorstadt: Advances Toward the Implantable Artificial Pancreas for Treatment of Diabetes. Diabetes Care (1998)–21. 3:444–450.

Stephen K. Hunter, Ye Wang, Carl P. Weiner, Jennifer Niebyl: Encapsulated β–islet cells as a bioartificial pancreas to treat insulin–dependent diabetes during pregnancy. Am. J. Obstet Gynecol, (1997) 177. 4:746–752.

Robert S. Dinsmoor: Islet Cell Transplantation: Working Toward a Cure, Children with Diabetes 1999. 19:34:38. Feb. 20.

Eastman RC, Javitt JC, Herman WH et al: Models of complications of type 2 diabetes: II. Analysis of the health benefits and cost–effectiveness of treating type 2 diabetes with the goal of normoglycemia. Diabetes Care 20:735–744, 1997.

The DCCT Study Group: Resource utilization and cost of care in the Diabetes Control and Complications Trial. Diabetes Care 18:1468–1478, 1995.

Hisako Oghawara, Sachiko Hiroteni, Jun–icki Miyazaki, Satoshi Teraoka: Membrane Immunoisolation of a Diffusion Chamber for a Bioartificial Pancreas. Artif. Organs, 22, 9:788–794, 1998.

M. Ahn, E. Chang, G. Chu, C.F. Barker, J.F. Markmann: Cellular Requirements for Pancreatic Islet Xenograft Rejection. Transplant Proc. 27, 6:3302–3303, 1995.

J.X. Wu. J. Tai, S.C. Cheung, W.J. Tze: Assessment of the Protective Effect of Uncoated Alginate Microspheres. Transplant Proc. 29,2146–2147, 1997.

E.J. Woods, J.R.T. Lakey, M.A.J. Zieger, J. Liu, D. Nelson, J.K. Critser: Permeability Characteristics of Microencapsulated Pancreatic Islets. Transplant Proc. 29,2148. 1997.

E. Rolland, E. Muscat, L. Mohadjer, P. Prevost: Insulin Secretion of Free and AN69 Encapsulated Islets. Transplant Proc. 29,2140–2141, 1997.

* cited by examiner

IMPLANTABLE BIOARTIFICIAL ACTIVE SECRETION SYSTEM

CROSS-REFERENCE TO RELATED APPLICATIONS (Not Applicable).

STATEMENT RE: FEDERALLY SPONSORED RESEARCH/DEVELOPMENT (Not Applicable).

BACKGROUND OF THE INVENTION

The present invention relates in general to implantable devices for providing medically required treatment regimens over a period of time, and in particular to an implantable bioartificial active secretion system comprising live secretory cells providing a physiologically-required secretion to a living-being host patient in response to specific respective needs of the patient as determined by the live secretory cells in response to physiological make-up of host tissue fluid in contact with the secretory cells.

Natural production of numerous agents, metabolites, enzymes, and other secretions occur within a living being host as physiological events take place. One such event is the metabolism of carbohydrates which is controlled mainly by insulin which is produced by beta cells of the islets of Langerhans within the pancreas. In addition to its principal role in carbohydrate metabolism, insulin also significantly affects lipid, protein, and mineral metabolism in addition to the metabolism of carbohydrates prior to their ultimate break-down to glucose. When efficient insulin production by the pancreas is inhibited or terminated and therefore insufficient, as occurs substantially in Type I diabetes, for example, where immune cells of the host infiltrate the islets of Langerhans and eventually destroy the beta cells by T-cell-mediated mechanisms, insulin from another source must be provided or the affected individual will suffer from many severe consequences of diabetes mellitus.

Prior-art approaches for providing insulin to maintain proper plasma glucose concentrations are numerous. One of the most commonly employed is the injection of insulin into the patient a plurality of times daily in response to plasma-glucose monitoring. Subcutaneous injection is a usual insulin introduction route, but is flawed and/or dis-favored for several reasons. In particular, injection administration is limited because there is no direct feedback between blood glucose level and the dosage of insulin. In addition, there is poor patient acceptance, significant absorption variability among patients, potential overdosing resulting in hyperinsulinemia/hypoglycemia, potential underdosing resulting in hypoinsulinemia/hyperglycemia, formation of anti-insulin antibodies, hypersensitivity reactions due to insulin formulations, and other untoward occurrences. Relatively new jet injector devices, as opposed to traditional syringes, do not appreciably avoid syringe-injection limitations as noted above. Orally administered insulin finds poor effectiveness because of the vast variability found in digestive processes and digestion states among patients.

Another prior art approach for providing insulin to patients is the provision of wearable or implantable insulin pumps which are pre-programmed and pre-loaded with insulin, therefore there is no direct feedback of optimal dosage. Unfortunately, however, these pumps can cause both mechanical and physiological problems for the patient. With respect to the former problem, these pumps can experience catheter blockage, infection, skin inflammation, erosion, local fluid accumulation, dislocation due to patient physical activity, and required regular refills of insulin usually at monthly or bimonthly intervals. With respect to the latter problem, presently available insulin pumps do not have reliable glucose sensors and therefore are unable to precisely dispense a needed insulin quantity for proper plasma-glucose level maintenance.

Yet another prior art approach for treating insulin deficiency is the transplantation of pancreatic beta cells to the pancreas, liver, muscles, or peritoneal cavity of the patient, or the transplantation of an entire donor-pancreas as a replacement. Such an approach, however, many times is not practical because of recipient immune-rejection, limited availability of donor organs, and other restraints on patient acceptance.

In view of the above inability of prior art approaches to artificially provide a natural imitation of a physiological secretion, it is apparent that a highly important need is present first for sensing an in vivo need for a secretory product, and second for fulfilling that need by providing an appropriate quantity of secretory product. Accordingly, a primary object of the present invention is to provide an implantable bioartificial active secretion system for providing, in vivo, a physiological secretion necessary for functionality of a physiologic activity dependent upon that secretion.

Another object of the present invention is to provide an implantable bioartificial active secretion system wherein physiologically active, autonomously functioning, live secretory cells for producing the physiological secretion are protected from immune destruction by the host while sensing and responding to functional need.

Still another object of the present invention is to provide an implantable bioartificial active secretion system wherein tissue fluid of the host is introduced to the live secretory cells for cell-secretion uptake and subsequent delivery for distribution within the host.

These and other objects of the present invention will become apparent throughout the description thereof that now follows.

BRIEF SUMMARY OF THE INVENTION

The present invention is an implantable bioartificial active secretion system for providing a physiological secretion necessary for functionality of a physiologic activity of a living-being host. The system first includes a housing having an inlet with an external opening thereto and an outlet with an external opening therefrom. This housing is implantable at least partially within the host such that the inlet and outlet openings are positionable in fluidic communication with tissue fluid of the host and the tissue fluid can be received into the housing and thereafter dispensed from the housing. A chamber is disposed within the housing between the inlet and outlet and in communication therewith, and contains a plurality of physiologically active, autonomously functioning, live secretory cells for producing the physiological secretion. Also disposed within the housing is a periodically-operating pump apparatus for drawing initial tissue fluid through the inlet from the host for contact with the physiologically active cells within the chamber for pick up and regulation of the physiological secretion, and for dispensing resulting tissue fluid bearing the physiological secretion through the outlet and into the host. Finally, inlet and outlet filter systems in operational communication with the external openings of the inlet and outlet have openings therethrough sized for prohibiting passage of immune system cells, immunoglobulins, and complement system components of the host.

The tissue fluid drawn to be in contact with the live secretory cells must generally reflect host requirements for the particular physiological secretion. Thus, in treating diabetes for example, peritoneal fluid is drawn since it is known that peritoneal fluid reflects blood glucose levels, whereby peritoneal fluid contacts secretory cells that are pancreatic beta cells which produce insulin for peritoneal-fluid uptake and return for routing to regulate such glucose levels. The secretory cells preferably are encapsulated with a permeable medium through which cellular nutrient as well as cellular metabolic waste can pass and likewise through which the physiological secretion can pass, but not through which immune system cells can pass on the off-chance that such cells passed through the inlet filter. Encapsulation increases the loading density of the cells and their surface interaction with the fluid. Depending upon the specific application, secretory-cell life span many times can be up to about two years, after which time replacement cells are introduced.

The pump apparatus preferably includes a plurality of sequentially disposed, peristaltic-like activated and deactivated, elasticized pump tubes for peristaltic-like moving therewithin the initial tissue fluid and the tissue fluid bearing the physiological secretion through the housing. Simultaneously, the preferred arrangement of the plurality of secretory cells is such that sub-pluralities thereof are disposed on a tray, a plurality of trays are situated into a column, and a plurality of columns are horizontally spaced from each other with respective inter-column spaces there between wherein pump tubes are situated. Peristaltic-like pumping can be accomplished electromagnetically by a programmed controller disposed with the housing and thus implanted, or by a programmed controller situated outside the patient and in proximity to the implanted housing. In either configuration, power is intermittently applied to replicate peristaltic movement of tissue fluid through the pump tubes and thus in moving contact with the live secretory cells situated within the housing. The tissue fluid must reflect whether a need is present for the particular secretion provided by the secretory cells (e.g., glucose level for insulin-secreting cells), whereby the secretory cells will naturally respond to the conveyed need and automatically produce a quantity of secretion specific to this need as sensed by the secretory cells. This secretion is picked up by the tissue fluid as it contacts the secretory cells, and thereafter is delivered within the host. Finally, when the tissue fluid indicates less need for the secretion (e.g., the required activity of the secretion has been completed for the time being), such reduced need is sensed by the secretory cells as the tissue fluid continues in contact therewith, and the secretory activity naturally ceases.

As is apparent, the implantable bioartificial active secretion system here defined significantly replicates natural metabolic function by employing live secretory cells as both sensor and provider of physiologic balance. Such live-cell employment eliminates external guess work with respect to quantity and timing of secretion-product injection or other type introduction since actual cells make a natural determination of need followed by a natural production and natural release of an exactly-necessary quantity of the secretory product.

BRIEF DESCRIPTION OF THE DRAWINGS

An illustrative and presently preferred embodiment of the invention is shown in the accompanying drawings in which.

DETAILED DESCRIPTION OF THE PREFERRED EMBODIMENT

Figure 1:
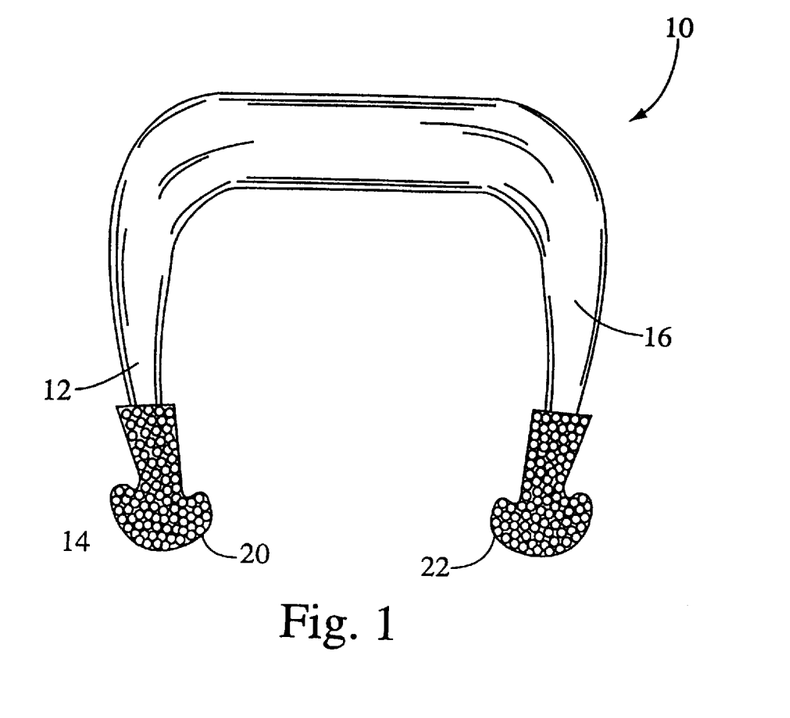
FIG. 1 is a top plan view of an implantable bioartificial active secretion system housing.
Figure 2:
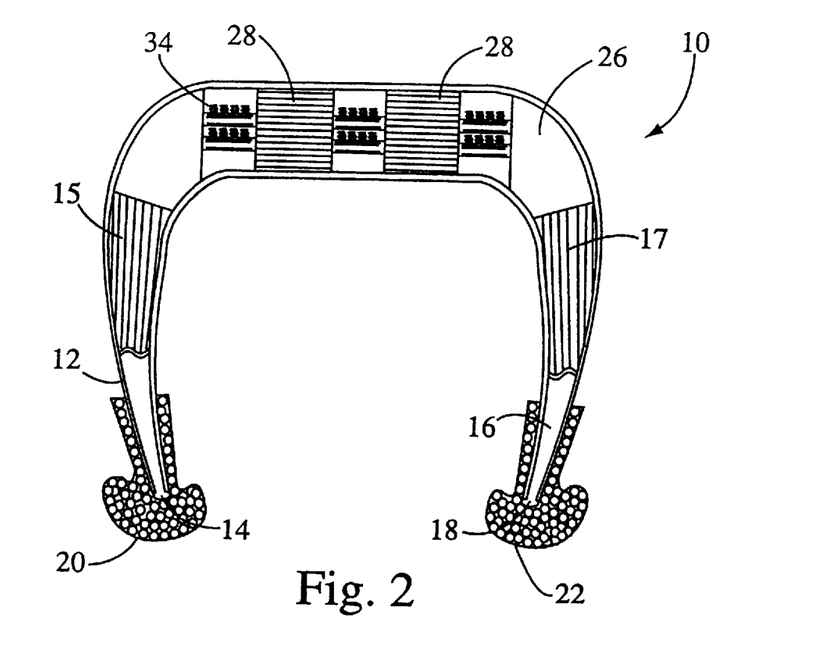
FIG. 2 is a top plan cut-away view of the housing of FIG. 1.
Figure 3:
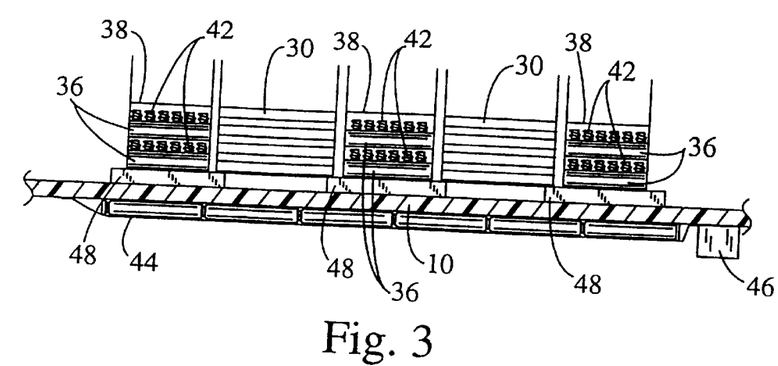
FIG. 3 is an enlarged side elevation view of the secretion system.
Figure 4A:
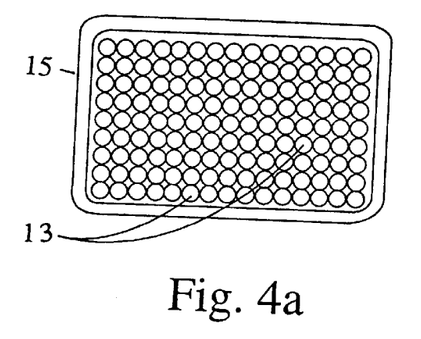
FIG. 4a is an end elevation view in section of a first configuration of a nano-capillary filtration bundle.
Figure 4B:
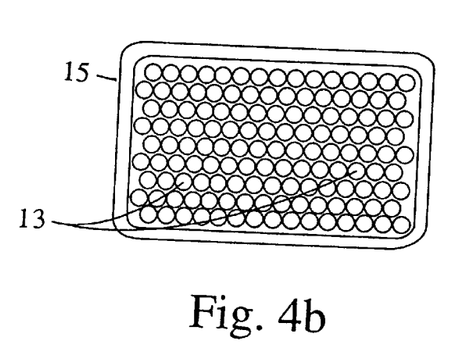
FIG. 4b is an end elevation view in section of a second configuration of a nano-capillary filtration bundle.
Figure 5:
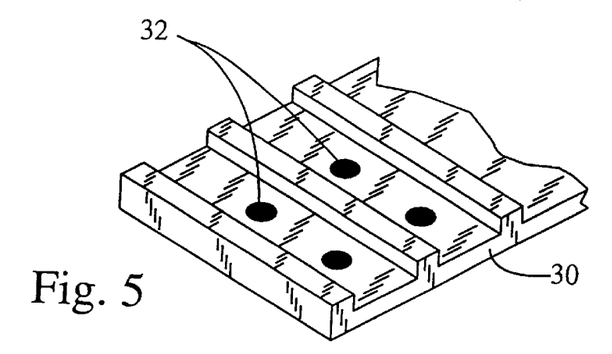
FIG. 5 is a partial perspective view of a tray containing secretory cells.

Referring to FIGS. 1–6a, an implantable bioartificial active secretion system housing 10 has an inlet 12 with an external inlet opening 14 thereto and an outlet 16 with an external outlet opening 18 therefrom, with each outlet 18, 16 having respectively therewith an inlet external filter 20 (shown in FIG. 1), an outlet external filter 22 (shown in FIGS. 1 and 2), and nano-capillary bundles 15, 17 therewithin (shown in FIGS. 2 and 4). The external filters 20, 22 function as prefilters that control inflow and outflow of fluids and have apertures sized to address entry of larger immune cells of the host. Liquids have generally unimpeded access through the filters 20, 22 while the preferred configuration of a mushroom-shape tip permits easy anchoring without tissue damage as the lower border of the mushroom configuration hooks into, for example, the wall of the peritoneal cavity of the host. Additionally, the configuration of the external filters 20, 22 functions to prevent clogging of the nano-capillary bundles 15, 17 and to provide insulin distribution. The nano-capillary bundles 15, 17 are constructed of glass or silica for filtration protection against entry of immune system cells, immunoglobulins, and complement system components of a host living being. As illustrated in FIGS. 4a and 4b, capillaries 13 of the bundles 15 (and 17) can be arranged in a quadrangular configuration (FIG. 4a) or in triangular configuration (FIG. 4b) in reference to each other. The housing 10 and external filters 20, 22 are fabricated of a biocompatible polymer as known in the art.

Figure 6A:
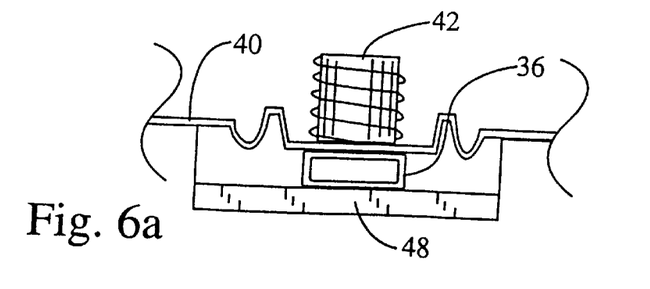
FIG. 6a is an end elevation view of a peristaltic pump mechanism.
Figure 6B:
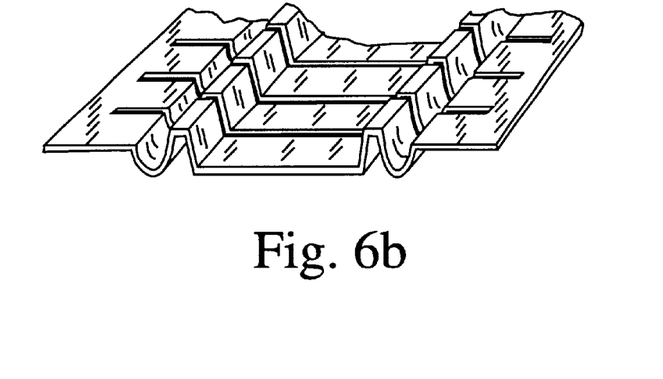
FIG. 6b is a perspective view of a portion of a memory alloy sheet.

Disposed within the housing 10 and in fluidic communication with the inlet 12 and outlet 16 is a chamber 26. Within the chamber 26 are housed a plurality of columns 28 of trays 30 wherein each tray 30 has thereon a sub-plurality of insulin secretory cells 32 such as provided by islet of Langerhans beta-cells or by pancreatic tissue cumulative to a plurality of such secretory cells 32 disbursed among the several trays 30 throughout the chamber 26. Situated adjacent each column 28 of trays 30 are respective elasticized pump tubes 36 preferably of rectangular cross-section as shown in FIG. 6a, each in fluidic communication with the trays 30 of the columns 28 on either horizontal side. Between the tubes 36 are respective electromagnetically-driven peristaltic pump mechanism members 38 for moving fluid (liquid) through the housing 10. Each member 38 includes a series of inductor coils 42 disposed above each respective tube 36 as particularly shown in FIG. 3. Immediately below the tubes 36 are permanent magnets 48, while immediately outside the housing 10 is a conventional battery pack 44 with standard wiring (not shown) leading to the inductor coils 42. A standard microprocessor 46 is programmed to provide sequentially-timed, intermittent, electrical charge to the inductor coils 42 whereby, upon power application, the tubes 36 below the respective inductor coils 42 have pressure exerted thereon because of attraction of the inductor coils 42 to the permanent magnets 48 to thereby compress these tubes 36 and force fluid therein through the tubes 36 to a subsequent column 28 of trays 30 for direct contact with the secretory cells 32 of respective trays 30 so contacted. Once compression of the tubes 36 has occurred, electrical charge to the involved inductor coils 42 is discontinued and the so-compressed tubes 36 expand to their original configuration while simultaneously creating suction to draw fluid from a preceding column 28 of trays 30 therein for a subsequent repeat of the sequential pumping as above described. A sheet 40 (FIGS. 6a and 6b) of non-magnetic memory alloy (e.g. nickel-titanium) typically is situated between the inductor coils 42 and tubes 36 such that the alloy is electromagnetically forced toward the permanent magnets 48 (and therefore the capillary tubes 36) to accomplish uniform compression of the tubes 36 during pumping activity. Cessation of electrical power to the involved inductor coils 42 withdraws the coils 42 from movement-attraction to the permanent magnets, and the memory alloy sheet 40 returns to its original non-distorted configuration. As illustrated in FIGS. 6a and 6b, the sheet 40 preferably is cross-sectionally shaped to enhance collapse against the tube 36 upon application of charge in the coils 42.

Figure 7:
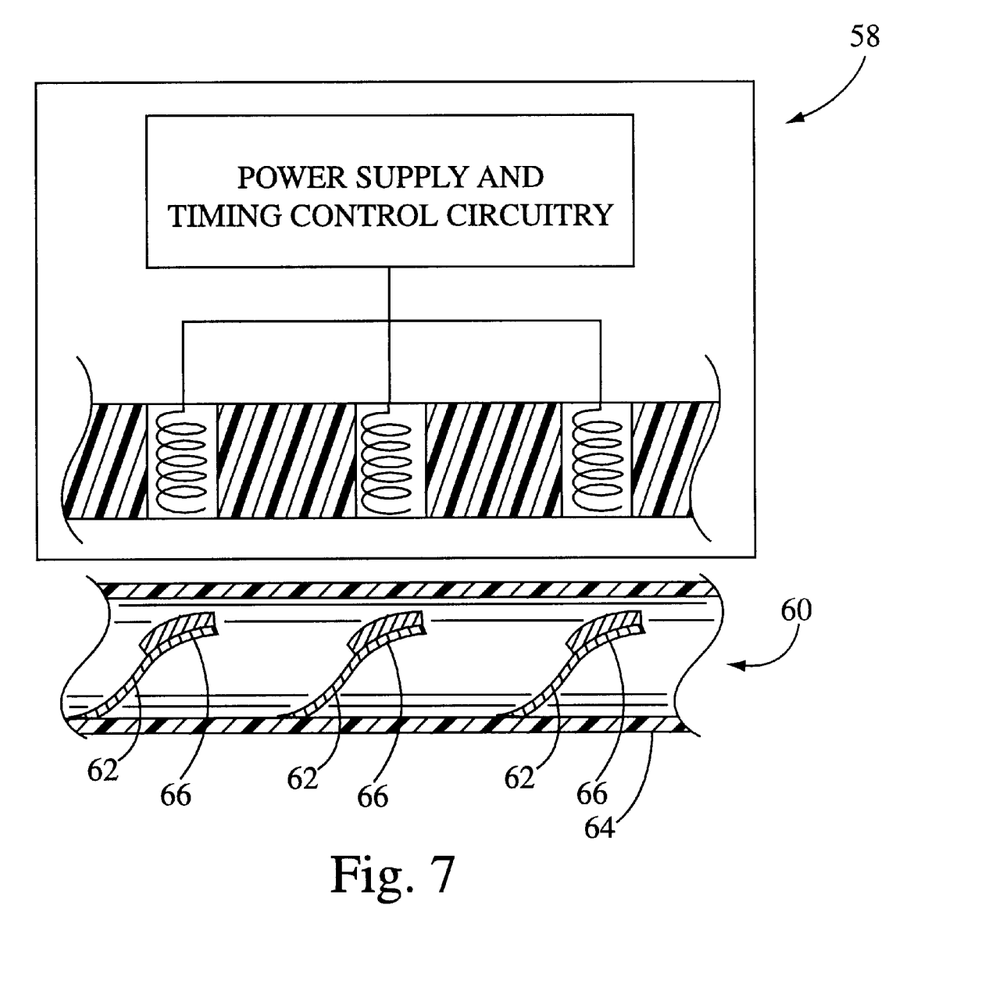
FIG. 7 is a partial side elevation view in section of an exteriorly powered secretion system.

While the embodiment described above with respect to FIGS. 1–6 has an integral power source, a second embodiment, illustrated in FIG. 7, provides for an externally-disposed, wearable power source 58 operating an internally-disposed system substantially identical to the system of the first embodiment except for non-presence of an implanted electrical power source and for construction of the pump assembly. In particular, with respect to the latter, FIG. 7 illustrates construction of one version of the pump tube 60 which includes a series of dielectric arms 62 extending from the floor 64 of the tube 60, with each such arm 62 having applied at its distal end a magnetic alloy or permalloy coating 66. When the power source 58 is activated, the magnetic flux thereby generated causes the dielectric arms 62 within the tube 60 to move toward the flux. Subsequently, when flux generation is discontinued, the arms 62 return to their original positions. Control circuitry of the power source 58 is such that sequential arm movements occur and thereby move fluid with a sweeping action through the tube 60 for contact with secretory cells as earlier described in connection with the first embodiment.

Operability is here non-limitedly exemplified in the physiologically beneficial delivery-on-demand of insulin for glucose metabolism within a patient suffering from Type I diabetes. Particularly, the system housing 10 functions in the capacity of an artificial pancreas and is implanted at a site within the peritoneal cavity such that peritoneal fluid can enter the housing 10. The housing 10 can be located subcutaneously and be anchored to the anterolateral region of the iliac crest bone by a bone anchor system as known in the art with catheter penetration through the peritoneal fascia and into the peritoneal cavity. This placement permits relatively easy, rapid, and complete retrieval in the event of any implant failure or malfunction. Implantation into the anterolateral subcutane abdominal region is carried out under local anesthesia. It is to be noted that peritoneal fluid is chosen for insulin-need determination because a change of glucose concentration in peritoneal fluid is in the same direction, same amount, and relatively same time factor as in blood. The peritoneal fluid travels through the inlet filter 20, inlet opening 14, and nano-capillary bundle 15 within the inlet 12 to the chamber 26 for entry into a first row 34 of pump tubes 36 and subsequent periodic pumping action that provides continuous microcirculation and drives the fluid to a first column 28 of trays 30 for contact with insulin secretory cells 32 which can be present as beta-cells or as tissue as described above.

In the preferred embodiment, groups of cells 32 are gelled-alginate encapsulated in bead configurations each having a diameter from about 50 to about 200 microns, with total count for the entire chamber 26 of at least about 1,000,000 cells. Each tray 30 preferably is fabricated of silicon or quartz material with wells etched into the surface for housing the secretory cells 32. The trays 30 preferably are clamped into stack configurations and are removable and replaceable as secretory cell life eventually expires. Movement of the peritoneal fluid continues through the chamber 26 for contact with each successive column 28 of trays 30 bearing the insulin secretory cells 32, as these secretory cells 32 naturally react to the glucose level of the peritoneal fluid and naturally secrete insulin into the peritoneal fluid as determined by the secretory cells 32 to be needed for proper glucose metabolism. Additionally, oxygen and nutrients are passed to the secretory cells 32 while metabolic waste from the secretory cells 32 passes into the peritoneal fluid. Upon completion of travel through the chamber 26, the peritoneal fluid moves to the outlet 16, through the nano-capillary bundle 17, external outlet opening 18 and outlet filter 22 for final reintroduction into the peritoneal cavity and final delivery to the circulatory system through normal and on-going routing for insulin delivery and use as well as elimination of secretory-cell waste products. Secretory-cell life spans are, of course, dependent upon a number of factors including proper nutrition and oxygen delivery, waste product removal, and extent of secretion called for by the host being. When cell effectiveness diminishes or ceases, however, the housing 10 is relatively easily retrieved and the columns 28 of trays 30 are easily removed and replaced by fresh units, with the housing 10 then returned to its implanted site.

As is apparent from the above description, the secretion system here defined bioartificially emulates a naturally occurring secretion system by providing live secretion-producing cells for sensing and producing secretions at levels naturally determined because of such live authenticity. In addition to such implantation of secretion-producing cells, other media, including drugs, medicines, and/or enzymes, for treating or preventing diseases in accord with physiological demands, can likewise be administered by employing the system here described and within which the chosen media is placed. Thus, while these illustrative and presently preferred embodiments of the invention have been described in detail herein, it is to be understood that the inventive concepts may be otherwise variously embodied and employed and that the appended claims are intended to be construed to include such variations except insofar as limited by the prior art.

What is claimed is:

1. An implantable bioartificial active secretion system for providing a physiological regulating secretion necessary for functionality of a physiologic activity of a living-being host, the system comprising:

a) a housing having an inlet with an external opening thereto and an outlet with an external opening therefrom, said housing implantable at least partially within the host such that the inlet and outlet openings are positionable in fluidic communication with tissue fluid of the host for receiving into and dispensing from the housing said tissue fluid;

b) a chamber disposed within the housing between the inlet and outlet and in communication therewith, said chamber having therein a plurality of physiologically active, autonomously functioning, live secretory cells for producing the physiological secretion;

c) a periodically operating pump apparatus for drawing initial tissue fluid through the inlet from the host for contact with the physiologically active cells within the chamber for pick up of the physiological regulating secretion, and for dispensing resulting tissue fluid bearing said physiological secretion through the outlet and into the host; and d) an inlet filter in operational communication with the external opening of the inlet and disposed upstream of the chamber, said inlet filter having interstices therethrough sized for prohibiting passage into the chamber of immune system cells of the host.

2. An implantable bioartificial active secretion system as claimed in claim 1 wherein the pump apparatus comprises a plurality of sequentially disposed, sequentially peristaltic-like activated pump tubes for peristaltic-like moving within said tubes the initial tissue fluid and the tissue fluid bearing the physiological secretion through the housing.

3. An implantable bioartificial active secretion system as claimed in claim 1 additionally comprising an outlet filter in operational communication with the external opening of the outlet and disposed downstream of the chamber, said outlet filter having interstices therethrough sized for prohibiting passage into the chamber of immune system cells of the host.

4. An implantable bioartificial active secretion system for providing a physiological secretion necessary for functionality of a physiologic activity of a living-being host, the system comprising:

a) a housing having an inlet with an external opening thereto and an outlet with an external opening therefrom, said housing implantable at least partially within the host such that the inlet and outlet openings are positionable in fluidic communication with peritoneal fluid within a peritoneal cavity of the host for receiving into and dispensing from the housing said peritoneal fluid;

b) a chamber disposed within the housing between the inlet and outlet and in communication therewith, said chamber having therein a plurality of physiologically active, autonomously functioning, live secretory cells for producing the physiological secretion;

c) a periodically operating pump apparatus disposed for drawing initial peritoneal fluid through the inlet from the peritoneal cavity for contact with the physiologically active cells within the chamber for pick up of the physiological secretion, and for dispensing resulting peritoneal fluid bearing said physiological regulating secretion through the outlet and into the peritoneal cavity; and d) an inlet filter in operational communication with the external opening of the inlet and disposed upstream of the chamber, said inlet filter having interstices therethrough sized for prohibiting passage into the chamber of immune system agents and cells, immunoglobulins, and complement system components of the host.

5. An implantable bioartificial active secretion system as claimed in claim 4 wherein the pump apparatus comprises a plurality of sequentially disposed, sequentially peristaltic-like activated pump tubes for peristaltic-like moving within said tubes the initial peritoneal fluid and the peritoneal fluid bearing the physiological secretion through the housing.

6. An implantable bioartificial active secretion system as claimed in claim 4 additionally comprising an outlet filter in operational communication with the external opening of the outlet and disposed downstream of the chamber, said outlet filter having interstices therethrough sized for prohibiting passage into the chamber of immune system agents, cells, immunoglobulins, and complement system components of the host.

7. An implantable bioartificial active secretion system for providing insulin as necessary for metabolism of glucose within a living-being host, the system comprising:

a) a housing having an inlet with an external opening thereto and an outlet with an external opening therefrom, said housing implantable at least partially within the host such that the inlet and outlet openings are positionable in fluidic communication with tissue fluid of the host for receiving into and dispensing from the housing said tissue fluid;

b) a chamber disposed within the housing between the inlet and outlet and in communication therewith, said chamber having therein a plurality of physiologically active, autonomously functioning, live secretory cells for producing insulin;

c) a periodically operating pump apparatus for drawing initial tissue fluid through the inlet from the host for contact with the physiologically active cells within the chamber for pick up of insulin, and for dispensing resulting tissue fluid bearing said insulin through the outlet and into the host; and d) an inlet filter in operational communication with the external opening of the inlet and disposed upstream of the chamber, said inlet filter having interstices therethrough sized for prohibiting passage into the chamber of immune system agents and cells, immunoglobulins, and complement system components of the host.

8. An implantable bioartificial active secretion system as claimed in claim 7 wherein the pump apparatus comprises a plurality of sequentially disposed, sequentially peristaltic-like activated pump tubes for peristaltic-like moving within said tubes the initial tissue fluid and the tissue fluid bearing insulin through the housing.

9. An implantable bioartificial active secretion system as claimed in claim 7 additionally comprising an outlet filter in operational communication with the external opening of the outlet and disposed downstream of the chamber, said outlet filter having interstices therethrough sized for prohibiting passage into the chamber of immune system cells, immunoglobulins, and complement system components of the host.

10. An implantable bioartificial active secretion system for providing insulin necessary for carbohydrate metabolism within a living-being host, the system comprising:

a) a housing having an inlet with an external opening thereto and an outlet with an external opening therefrom, said housing implantable at least partially within the host such that the inlet and outlet openings are positionable in fluidic communication with peritoneal fluid inside a peritoneal cavity of the host for receiving into and dispensing from the housing said peritoneal fluid;

b) a chamber disposed within the housing between the inlet and outlet and in communication therewith, said chamber having therein a plurality of physiologically active, autonomously functioning, live secretory cells for producing insulin;

c) a periodically operating pump apparatus regulated by a controller for drawing initial peritoneal fluid through the inlet from the peritoneal cavity for contact with the physiologically active cells within the chamber for pick up of regulating insulin, and for dispensing resulting peritoneal fluid bearing said insulin through the outlet and into the peritoneal cavity; and d) an inlet filter in operational communication with the external opening of the inlet and disposed upstream of the chamber, said inlet filter having interstices therethrough sized for prohibiting passage into the chamber of immune system cells, immunoglobulins, and complement system components of the host.

11. An implantable bioartificial active secretion system as claimed in claim 10 wherein the pump apparatus comprises a plurality of sequentially disposed, sequentially peristaltic-like activated, elasticized pump tubes for peristaltic-like moving within said tubes the initial peritoneal fluid and the peritoneal fluid bearing insulin through the housing.

12. An implantable bioartificial active secretion system as claimed in claim 10 additionally comprising an outlet filter in operational communication with the external opening of the outlet and disposed downstream of the chamber, said outlet filter having interstices therethrough sized for prohibiting passage into the chamber of immune system agents and cells, immunoglobulins, and complement systemcomponents of the host.

13. An implantable bioartificial active secretion system as claimed in claim 10 wherein the physiologically active secretory pancreatic beta-islet cells are provided from human allogenic and/or xenogenic and/or gene development technology sources.

14. An implantable bioartificial active secretion system as claimed in claim 10 wherein the physiologically active secretory cells are provided as pancreatic islet beta cells.

15. An implantable bioartificial active secretion system as claimed in claim 10 wherein the periodically operating pump apparatus is driven by electromagnetic impulse energy.

16. An implantable bioartificial active secretion system as claimed in claim 15 wherein the controller is programmable and regulates administration of said electromagnetic pulse energy.

17. An implantable bioartificial active secretion system as claimed in claim 16 wherein said controller is integral with the housing.

18. An implantable bioartificial active secretion system as claimed in claim 16 wherein said controller is remote from the housing.

19. An implantable bioartificial active secretion system for providing a physiological secretion necessary for functionality of a physiologic activity of a living-being host, the system comprising:

a) a housing having an inlet with an external opening thereto and an outlet with an external opening therefrom, said housing implantable at least partially within the host such that the inlet and outlet openings are positionable in fluidic communication with tissue fluid of the host for receiving into and dispensing from the housing said tissue fluid;

b) a chamber disposed within the housing between the inlet and outlet and in communication therewith, said chamber having therein a plurality of physiologically active, autonomously functioning, live secretory cells for producing the physiological secretion, the plurality of physiologically active secretory cells being divided into sub-pluralities whereby each sub-plurality of physiologically active secretory cells is disposed on a tray, a plurality of such trays being situated into a column, and a plurality of such columns being horizontally spaced from each other with respective inter-column spaces there between;

c) a periodically operating pump apparatus for drawing initial tissue fluid through the inlet from the host for contact with the physiologically active cells within the chamber for pick up of the physiological secretion, and for dispensing resulting tissue fluid bearing said physiological secretion through the outlet and into the host; and d) an inlet filter in operational communication with the external opening of the inlet and disposed upstream of the chamber, said inlet filter having interstices therethrough sized for prohibiting passage into the chamber of immune system cells of the host.

20. An implantable bioartificial active secretion system as claimed in claim 19 wherein the pump apparatus comprises a plurality of sequentially disposed, persistaltic-like activated and deactivated, elasticized pump tubes for peristaltic-like moving within said tubes the initial tissue fluid and the tissue fluid bearing the physiological secretion through the housing.

21. An implantable bioartificial active secretion system as claimed in claim 19 wherein each sub-plurality of physiologically active secretory cells is encapsulated with a permeable medium through which nutrient for and metabolic waste from each cell can pass and through which said physiological secretion can pass.

22. An implantable bioartificial active secretion system for providing a physiological secretion necessary for functionality of a physiologic activity of a living-being host, the system comprising:

a) a housing having an inlet with an external opening thereto and an outlet with an external opening therefrom, said housing implantable at least partially within the host such that the inlet and outlet openings are positionable in fluidic communication with tissue fluid of the host for receiving into and dispensing from the housing said tissue fluid;

b) a chamber disposed within the housing between the inlet and outlet and in communication therewith, said chamber having therein a plurality of physiologically active, autonomously functioning, live secretory cells for producing the physiological secretion;

c) a periodically operating pump apparatus for drawing initial tissue fluid through the inlet from the host for contact with the physiologically active cells within the chamber for pick up of the physiological secretion, and for dispensing resulting tissue fluid bearing said physiological secretion through the outlet and into the host; and d) an inlet filter in operational communication with the external opening of the inlet and disposed upstream of the chamber, said inlet filter having interstices therethrough sized for prohibiting passage into the chamber of immune system cells of the host, the filter comprising at least one nano-capillary bundle constructed of glass or silica through which entering tissue fluid must pass.

23. An implantable bioartificial active secretion system for providing a physiological secretion necessary for functionality of a physiologic activity of a living-being host, the system comprising:
  a) a housing having an inlet with an external opening thereto and an outlet with an external opening therefrom, said housing implantable at least partially within the host such that the inlet and outlet openings are positionable in fluidic communication with tissue fluid of the host for receiving into and dispensing from the housing said tissue fluid;
  b) a chamber disposed within the housing between the inlet and outlet and in communication therewith, said chamber having therein a plurality of physiologically active, autonomously functioning, live secretory cells for producing the physiological secretion;
  c) a periodically operating pump apparatus for drawing initial tissue fluid through the inlet from the host for contact with the physiologically active cells within the chamber for pick up of the physiological secretion, and for dispensing resulting tissue fluid bearing said physiological secretion through the outlet and into the host;
  d) an inlet filter in operational communication with the external opening of the inlet and disposed upstream of the chamber, said inlet filter having interstices therethrough sized for prohibiting passage into the chamber of immune system cells of the host; and
  e) an outlet filter in operational communication with the external opening of the outlet and disposed downstream of the chamber, said outlet filter having interstices therethrough sized for prohibiting passage into the chamber of immune system cells of the host, the outlet filter comprising at least one nano-capillary bundle constructed of glass or silica through which exiting tissue fluid must pass.

24. An implantable bioartificial active secretion system for providing a physiological secretion necessary for functionality of a physiologic activity of a living-being host, the system comprising:
  a) a housing having an inlet with an external opening thereto and an outlet with an external opening therefrom, said housing implantable at least partially within the host such that the inlet and outlet openings are positionable in fluidic communication with tissue fluid of the host for receiving into and dispensing from the housing said tissue fluid;
  b) a chamber disposed within the housing between the inlet and outlet and in communication therewith, said chamber having therein a plurality of physiologically active, autonomously functioning, live secretory cells for producing the physiological secretion;
  c) a periodically operating pump apparatus for drawing initial tissue fluid through the inlet from the host for contact with the physiologically active cells within the chamber for pick up of the physiological secretion, and for dispensing resulting tissue fluid bearing said physiological secretion through the outlet and into the host;
  d) an inlet filter in operational communication with the external opening of the inlet and disposed upstream of the chamber, said inlet filter having interstices therethrough sized for prohibiting passage into the chamber of immune system cells of the host; and
  e) an outlet filter in operational communication with the external opening of the outlet and disposed downstream of the chamber, said outlet filter having interstices therethrough sized for prohibiting passage into the chamber of immune system cells of the host, the outlet filter comprising capillaries of nano-capillary bundles arranged in quadrangular or triangular configuration in reference to each other.

25. An implantable bioartificial active secretion system as claimed in claim 24 wherein the filter comprises at least one nano-capillary bundle constructed of glass or silica through which entering tissue fluid must pass.

26. An implantable bioartificial active secretion system for providing a physiological secretion necessary for functionality of a physiologic activity of a living-being host, the system comprising:
  a) a housing having an inlet with an external opening thereto and an outlet with an external opening therefrom, said housing implantable at least partially within the host such that the inlet and outlet openings are positionable in fluidic communication with peritoneal fluid within a peritoneal cavity of the host for receiving into and dispensing from the housing said peritoneal fluid;
  b) a chamber disposed within the housing between the inlet and outlet and in communication therewith, said chamber having therein a plurality of physiologically active, autonomously functioning, live secretory cells for producing the physiological secretion, the plurality of physiologically active secretory cells being divided into sub-pluralities whereby each sub-plurality of physiologically active secretory cells is disposed on a tray, a plurality of such trays being situated into a column, and a plurality of such columns being horizontally spaced from each other with respective inter-column spaces there between;
  c) a periodically operating pump apparatus disposed for drawing initial peritoneal fluid through the inlet from the peritoneal cavity for contact with the physiologically active cells within the chamber for pick up of the physiological secretion, and for dispensing resulting peritoneal fluid bearing said physiological regulating secretion through the outlet and into the peritoneal cavity; and
  d) an inlet filter in operational communication with the external opening of the inlet and disposed upstream of the chamber, said inlet filter having interstices therethrough sized for prohibiting passage into the chamber of immune system agents and cells, immunoglobulins, and complement system components of the host.

27. An implantable bioartificial active secretion system as claimed in claim 26 wherein the pump apparatus comprises a plurality of sequentially disposed, peristaltic-like activated and deactivated, elasticized pump tubes for peristaltic-like moving within said tubes the initial peritoneal fluid and the peritoneal fluid bearing the physiological secretion through the housing.

28. An implantable bioartificial active secretion system as claimed in claim 26 wherein each sub-plurality of physiologically active secretory cells is encapsulated with a permeable medium through which nutrient for and metabolic waste from each cell can pass and through which said physiological secretion can pass.

29. An implantable bioartificial active secretion system for providing a physiological secretion necessary for functionality of a physiologic activity of a living-being host, the system comprising:
  a) a housing having an inlet with an external opening thereto and an outlet with an external opening therefrom, said housing implantable at least partially within the host such that the inlet and outlet openings are positionable in fluidic communication with peritoneal fluid within a peritoneal cavity of the host for receiving into and dispensing from the housing said peritoneal fluid;

b) a chamber disposed within the housing between the inlet and outlet and in communication therewith, said chamber having therein a plurality of physiologically active, autonomously functioning, live secretory cells for producing the physiological secretion;

c) a periodically operating pump apparatus disposed for drawing initial peritoneal fluid through the inlet from the peritoneal cavity for contact with the physiologically active cells within the chamber for pick up of the physiological secretion, and for dispensing resulting peritoneal fluid bearing said physiological regulating secretion through the outlet and into the peritoneal cavity;

d) an inlet filter in operational communication with the external opening of the inlet and disposed upstream of the chamber, said inlet filter having interstices therethrough sized for prohibiting passage into the chamber of immune system agents and cells, immunoglobulins, and complement system components of the host; and e) an outlet filter in operational communication with the external opening of the outlet and disposed downstream of the chamber, said outlet filter having interstices therethrough sized for prohibiting passage into the chamber of immune system agents, cells, immunoglobulins, and complement system components of the host, the outlet filter comprising nano-capillary bundle constructed of glass or silica through which exiting tissue fluid must pass.

30. An implantable bioartificial active secretion system for providing a physiological secretion necessary for functionality of a physiologic activity of a living-being host, the system comprising:

a) a housing having an inlet with an external opening thereto and an outlet with an external opening therefrom, said housing implantable at least partially within the host such that the inlet and outlet openings are positionable in fluidic communication with peritoneal fluid within a peritoneal cavity of the host for receiving into and dispensing from the housing said peritoneal fluid;

b) a chamber disposed within the housing between the inlet and outlet and in communication therewith, said chamber having therein a plurality of physiologically active, autonomously functioning, live secretory cells for producing the physiological secretion;

c) a periodically operating pump apparatus disposed for drawing initial peritoneal fluid through the inlet from the peritoneal cavity for contact with the physiologically active cells within the chamber for pick up of the physiological secretion, and for dispensing resulting peritoneal fluid bearing said physiological regulating secretion through the outlet and into the peritoneal cavity;

d) an inlet filter in operational communication with the external opening of the inlet and disposed upstream of the chamber, said inlet filter having interstices therethrough sized for prohibiting passage into the chamber of immune system agents and cells, immunoglobulins, and complement system components of the host; and e) an outlet filter in operational communication with the external opening of the outlet and disposed downstream of the chamber, said outlet filter having interstices therethrough sized for prohibiting passage into the chamber of immune system agents, cells, immunoglobulins, and complement system components of the host, the outlet filter comprising capillaries of nano-capillary bundles arranged in quadrangular or triangular configuration in reference to each other.

31. An implantable bioartificial active secretion system as claimed in claim 30 wherein each sub-plurality of physiologically active secretory cells is encapsulated with a permeable medium through which nutrient for and metabolic waste from each cell can pass and through which insulin can pass.

32. An implantable bioartificial active secretion system for providing insulin as necessary for metabolism of glucose within a living-being host, the system comprising:

a) a housing having an inlet with an external opening thereto and an outlet with an external opening therefrom, said housing implantable at least partially within the host such that the inlet and outlet openings are positionable in fluidic communication with tissue fluid of the host for receiving into and dispensing from the housing said tissue fluid;

b) a chamber disposed within the housing between the inlet and outlet and in communication therewith, said chamber having therein a plurality of physiologically active, autonomously functioning, live secretory cells for producing insulin, the plurality of physiologically active secretory cells being divided into sub-pluralities whereby each sub-plurality of physiologically active secretory cells is disposed on a tray, a plurality of such trays being situated into a column, and a plurality of such columns being horizontally spaced from each other with respective inter-column spaces there between;

c) a periodically operating pump apparatus for drawing initial tissue fluid through the inlet from the host for contact with the physiologically active cells within the chamber for pick up of insulin, and for dispensing resulting tissue fluid bearing said insulin through the outlet and into the host; and d) an inlet filter in operational communication with the external opening of the inlet and disposed upstream of the chamber, said inlet filter having interstices therethrough sized for prohibiting passage into the chamber of immune system agents and cells, immunoglobulins, and complement system components of the host.

33. An implantable bioartificial active secretion system as claimed in claim 32 wherein the pump apparatus comprises a plurality of sequentially disposed, peristaltic-like activated and deactivated pump tubes for peristaltic-like moving within said tubes the initial tissue fluid and the tissue fluid bearing insulin through the housing, and further wherein each said inter-column space has disposed therein at least one said capillary-tubing bundle.

34. An implantable bioartificial active secretion system for providing insulin as necessary for metabolism of glucose within a living-being host, the system comprising:

a) a housing having an inlet with an external opening thereto and an outlet with an external opening therefrom, said housing implantable at least partially within the host such that the inlet and outlet openings are positionable in fluidic communication with tissue fluid of the host for receiving into and dispensing from the housing said tissue fluid;

b) a chamber disposed within the housing between the inlet and outlet and in communication therewith, said chamber having therein a plurality of physiologically active, autonomously functioning, live secretory cells for producing insulin;

c) a periodically operating pump apparatus for drawing initial tissue fluid through the inlet from the host for contact with the physiologically active cells within the chamber for pick up of insulin, and for dispensing resulting tissue fluid bearing said insulin through the outlet and into the host; and d) an inlet filter in operational communication with the external opening of the inlet and disposed upstream of the chamber, said inlet filter having interstices therethrough sized for prohibiting passage into the chamber of immune system agents and cells, immunoglobulins, and complement system components of the host, the filter comprising at least one nano-capillary bundle constructed of glass or silica through which entering tissue fluid must pass.

35. An implantable bioartificial active secretion system for providing insulin as necessary for metabolism of glucose within a living-being host, the system comprising:

a) a housing having an inlet with an external opening thereto and an outlet with an external opening therefrom, said housing implantable at least partially within the host such that the inlet and outlet openings are positionable in fluidic communication with tissue fluid of the host for receiving into and dispensing from the housing said tissue fluid;

b) a chamber disposed within the housing between the inlet and outlet and in communication therewith, said chamber having therein a plurality of physiologically active, autonomously functioning, live secretory cells for producing insulin;

c) a periodically operating pump apparatus for drawing initial tissue fluid through the inlet from the host for contact with the physiologically active cells within the chamber for pick up of insulin, and for dispensing resulting tissue fluid bearing said insulin through the outlet and into the host;

d) an inlet filter in operational communication with the external opening of the inlet and disposed upstream of the chamber, said inlet filter having interstices therethrough sized for prohibiting passage into the chamber of immune system agents and cells, immunoglobulins, and complement system components of the host; and e) an outlet filter in operational communication with the external opening of the outlet and disposed downstream of the chamber, said outlet filter having interstices therethrough sized for prohibiting passage into the chamber of immune system cells, immunoglobulins, and complement system components of the host, the outlet filter comprising at least one nano-capillary bundle constructed of glass or silica through which exiting tissue fluid must pass.

36. An implantable bioartificial active secretion system for providing insulin as necessary for metabolism of glucose within a living-being host, the system comprising:

a) a housing having an inlet with an external opening thereto and an outlet with an external opening therefrom, said housing implantable at least partially within the host such that the inlet and outlet openings are positionable in fluidic communication with tissue fluid of the host for receiving into and dispensing from the housing said tissue fluid;

b) a chamber disposed within the housing between the inlet and outlet and in communication therewith, said chamber having therein a plurality of physiologically active, autonomously functioning, live secretory cells for producing insulin;

c) a periodically operating pump apparatus for drawing initial tissue fluid through the inlet from the host for contact with the physiologically active cells within the chamber for pick up of insulin, and for dispensing resulting tissue fluid bearing said insulin through the outlet and into the host;

d) an inlet filter in operational communication with the external opening of the inlet and disposed upstream of the chamber, said inlet filter having interstices therethrough sized for prohibiting passage into the chamber of immune system agents and cells, immunoglobulins, and complement system components of the host; and e) an outlet filter in operational communication with the external opening of the outlet and disposed downstream of the chamber, said outlet filter having interstices therethrough sized for prohibiting passage into the chamber of immune system cells, immunoglobulins, and complement system components of the host, the outlet filter comprising capillaries of nano-capillary bundles arranged in quadrangular or triangular configuration in reference to each other.

37. An implantable bioartificial active secretion system for providing insulin necessary for carbohydrate metabolism within a living-being host, the system comprising:

a) a housing having an inlet with an external opening thereto and an outlet with an external opening therefrom, said housing implantable at least partially within the host such that the inlet and outlet openings are positionable in fluidic communication with peritoneal fluid inside a peritoneal cavity of the host for receiving into and dispensing from the housing said peritoneal fluid;

b) a chamber disposed within the housing between the inlet and outlet and in communication therewith, said chamber having therein a plurality of physiologically active, autonomously functioning, live secretory cells for producing insulin, the plurality of physiologically active secretory cells being divided into sub-pluralities whereby each sub-plurality of physiologically active secretory cells being disposed on a tray, a plurality of such trays being situated into a column, and a plurality of such columns being horizontally spaced from each other with respective inter-column spaces there between;

c) a periodically operating pump apparatus regulated by a controller for drawing initial peritoneal fluid through the inlet from the peritoneal cavity for contact with the physiologically active cells within the chamber for pick up of regulating insulin, and for dispensing resulting peritoneal fluid bearing said insulin through the outlet and into the peritoneal cavity; and d) an inlet filter in operational communication with the external opening of the inlet and disposed upstream of the chamber, said inlet filter having interstices therethrough sized for prohibiting passage into the chamber of immune system cells, immunoglobulins, and complement system components of the host.

38. An implantable bioartificial active secretion system as claimed in claim 37 wherein the pump apparatus comprises a plurality of sequentially disposed, peristaltic-like activated and deactivated, elasticized pump tubes for peristaltic-like moving within said tubes the initial peritoneal fluid and the peritoneal fluid bearing insulin through the housing, and further wherein each said inter-column space has disposed therein at least one said capillary-tubing bundle.

39. An implantable bioartificial active secretion system as claimed in claim 37 wherein each sub-plurality of physiologically active secretory cells is encapsulated with a permeable medium through which nutrient for and metabolic waste from each cell can pass and through which said physiological secretion can pass.

40. An implantable bioartificial active secretion system for providing insulin necessary for carbohydrate metabolism within a living-being host, the system comprising:
  a) a housing having an inlet with an external opening thereto and an outlet with an external opening therefrom, said housing implantable at least partially within the host such that the inlet and outlet openings are positionable in fluidic communication with peritoneal fluid inside a peritoneal cavity of the host for receiving into and dispensing from the housing said peritoneal fluid;
  b) a chamber disposed within the housing between the inlet and outlet and in communication therewith, said chamber having therein a plurality of physiologically active, autonomously functioning, live secretory cells for producing insulin;
  c) a periodically operating pump apparatus regulated by a controller for drawing initial peritoneal fluid through the inlet from the peritoneal cavity for contact with the physiologically active cells within the chamber for pick up of regulating insulin, and for dispensing resulting peritoneal fluid bearing said insulin through the outlet and into the peritoneal cavity; and
  d) an inlet filter in operational communication with the external opening of the inlet and disposed upstream of the chamber, said inlet filter having interstices therethrough sized for prohibiting passage into the chamber of immune system cells, immunoglobulins, and complement system components of the host, the filter comprising at least one nano-capillary bundle constructed of glass or silica through which entering tissue fluid must pass.

41. An implantable bioartificial active secretion system for providing insulin necessary for carbohydrate metabolism within a living-being host, the system comprising:
  a) a housing having an inlet with an external opening thereto and an outlet with an external opening therefrom, said housing implantable at least partially within the host such that the inlet and outlet openings are positionable in fluidic communication with peritoneal fluid inside a peritoneal cavity of the host for receiving into and dispensing from the housing said peritoneal fluid;
  b) a chamber disposed within the housing between the inlet and outlet and in communication therewith, said chamber having therein a plurality of physiologically active, autonomously functioning, live secretory cells for producing insulin;
  c) a periodically operating pump apparatus regulated by a controller for drawing initial peritoneal fluid through the inlet from the peritoneal cavity for contact with the physiologically active cells within the chamber for pick up of regulating insulin, and for dispensing resulting peritoneal fluid bearing said insulin through the outlet and into the peritoneal cavity;
  d) an inlet filter in operational communication with the external opening of the inlet and disposed upstream of the chamber, said inlet filter having interstices therethrough sized for prohibiting passage into the chamber of immune system cells, immunoglobulins, and complement system components of the host; and
  e) an outlet filter in operational communication with the external opening of the outlet and disposed downstream of the chamber, said outlet filter having interstices therethrough sized for prohibiting passage into the chamber of immune system agents and cells, immunoglobulins, and complement system components of the host, the outlet filter comprising t least one nano-capillary bundle constructed of glass or silica through which exiting tissue fluid must pass.

42. An implantable bioartificial active secretion system for providing insulin necessary for carbohydrate metabolism within a living-being host, the system comprising:
  a) a housing having an inlet with an external opening thereto and an outlet with an external opening therefrom, said housing implantable at least partially within the host such that the inlet and outlet openings are positionable in fluidic communication with peritoneal fluid inside a peritoneal cavity of the host for receiving into and dispensing from the housing said peritoneal fluid;
  b) a chamber disposed within the housing between the inlet and outlet and in communication therewith, said chamber having therein a plurality of physiologically active, autonomously functioning, live secretory cells for producing insulin;
  c) a periodically operating pump apparatus regulated by a controller for drawing initial peritoneal fluid through the inlet from the peritoneal cavity for contact with the physiologically active cells within the chamber for pick up of regulating insulin, and for dispensing resulting peritoneal fluid bearing said insulin through the outlet and into the peritoneal cavity;
  d) an inlet filter in operational communication with the external opening of the inlet and disposed upstream of the chamber, said inlet filter having interstices therethrough sized for prohibiting passage into the chamber of immune system cells, immunoglobulins, and complement system components of the host; and
  e) an outlet filter in operational communication with the external opening of the outlet and disposed downstream of the chamber, said outlet filter having interstices therethrough sized for prohibiting passage into the chamber of immune system agents and cells, immunoglobulins, and complement system components of the host, the outlet filter comprising capillaries of nano-capillary bundles arranged in quadrangular or triangular configuration in reference to each other.

* * * * *